US009814755B2

(12) United States Patent
Hruby et al.

(10) Patent No.: US 9,814,755 B2
(45) Date of Patent: *Nov. 14, 2017

(54) METHODS FOR THE TREATMENT OF DEPRESSION AND ANXIETY

(71) Applicant: THE ARIZONA BOARD OF REGENTS ON BEHALF OF THE UNIVERSITY OF ARIZONA, Tucson, AZ (US)

(72) Inventors: Victor J. Hruby, Tucson, AZ (US); Minying Cai, Tucson, AZ (US); Horst Kessler, Schwalbach (DE)

(73) Assignee: THE ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/943,936

(22) Filed: Nov. 17, 2015

(65) Prior Publication Data
US 2017/0020953 A1   Jan. 26, 2017

Related U.S. Application Data

(63) Continuation-in-part of application No. PCT/US2015/035180, filed on Jun. 10, 2015, which is a continuation-in-part of application No. 14/300,991, filed on Jun. 10, 2014, now Pat. No. 9,290,539.

(60) Provisional application No. 62/242,850, filed on Oct. 16, 2015, provisional application No. 62/017,137, filed on Jun. 25, 2014.

(51) Int. Cl.
C07K 14/68 (2006.01)
C07K 7/06 (2006.01)
C07K 14/685 (2006.01)
A61K 8/64 (2006.01)
A61K 38/17 (2006.01)
A61K 38/12 (2006.01)
A61K 31/555 (2006.01)
A61K 38/10 (2006.01)
A61K 9/00 (2006.01)
A61K 47/24 (2006.01)
A61K 9/107 (2006.01)
A61K 9/70 (2006.01)
C07K 14/72 (2006.01)
C07K 7/08 (2006.01)

(52) U.S. Cl.
CPC ............ A61K 38/12 (2013.01); A61K 9/0014 (2013.01); A61K 9/107 (2013.01); A61K 9/7084 (2013.01); A61K 31/555 (2013.01); A61K 38/10 (2013.01); A61K 38/177 (2013.01); A61K 47/24 (2013.01); C07K 7/08 (2013.01); C07K 14/68 (2013.01); C07K 14/685 (2013.01); C07K 14/723 (2013.01)

(58) Field of Classification Search
None
See application file for complete search history.

(56) References Cited

U.S. PATENT DOCUMENTS

| 5,714,576 | A  | 2/1998  | Hruby et al.     |
|-----------|----|---------|------------------|
| 5,731,408 | A  | 3/1998  | Hadley et al.    |
| 5,830,994 | A  | 11/1998 | D'Hinterland et al. |
| 6,228,840 | B1 | 5/2001  | Wei et al.       |
| 6,350,430 | B1 | 2/2002  | Dooley et al.    |
| 7,045,503 | B1 | 5/2006  | McBride et al.   |
| 7,160,873 | B2 | 1/2007  | Magda et al.     |
| 7,582,610 | B2 | 9/2009  | Haskell-Luevano  |
| 2005/0037951 | A1 | 2/2005 | Blood et al.    |
| 2005/0038230 | A1 | 2/2005 | Sharma et al.   |
| 2005/0187164 | A1 | 8/2005 | Pinel           |
| 2007/0270411 | A1 | 11/2007 | Szewczyk et al. |
| 2009/0232838 | A1 | 9/2009  | Dong et al.     |
| 2010/0129319 | A1 | 5/2010  | Lindquist et al. |
| 2015/0037376 | A1 | 2/2015  | Seth et al.     |

FOREIGN PATENT DOCUMENTS

| WO | WO2005/079574 A1  | 9/2005  |
| WO | WO 2005-120588    | 12/2005 |
| WO | WO 2006/037188 A1 | 4/2006  |
| WO | WO 2008/071438 A2 | 6/2008  |
| WO | WO 2011-063367    | 5/2011  |

OTHER PUBLICATIONS

Kask et al., Endocrinology, 139: 5006-5014, 1998.*
Skinsight (http://www.skinsigh.com/diseaseList.htm, accessed Apr. 14, 2015).
Merck Manual (http://www.merckmanuals.com/professional/dermatologic-disorders/cancers-of-the-skin/melanoma, accessed Apr. 14, 2015).
Abdel-Malek (Melanoma prevention strategy based on using tetrapeptide a-MSH analogs that protect human melanocytes from UV-induced DNA damage and cytotoxicity; The FASEB Journal; 20, E888-E896 (2006).
Choi et al. (Elastic vesicles as topical/transdermal drug delivery systems; International Journal of Cosmetic Science, 2005, 27, 211-221).
Barkey NM et al., "Development of melanoma-targeted polymer micelles by conjugation of a Melanocortin 1 Receptor (MC 1 R) specific ligand" Journal of Medicinal Chemistry, 2011, 54(23):8078-8084.

(Continued)

Primary Examiner — Kimberly A. Ballard
Assistant Examiner — Stacey MacFarlane
(74) Attorney, Agent, or Firm — Nguyen & Tarbet Patent Law Firm

(57) ABSTRACT

Methods of treating a depressive disorder or an anxiety disorder in a subject in need of such treatment are described. A therapeutically effective amount of a composition comprising Ac-Nle$^4$-c[Asp$^5$-His$^6$-(NMe)D-Nal(2')$^7$-Arg$^8$-Trp$^9$-(NMe)Lys$^{10}$]-NH$_2$ (PEPTIDE 9), in a pharmaceutically acceptable carrier is administered to the subject. PEPTIDE 9 is a selective MC5R antagonist, in which administration thereof to the subject can treat the depressive or generalized anxiety disorder with clinical improvement observed in a relatively short time.

18 Claims, 2 Drawing Sheets

(56) References Cited

OTHER PUBLICATIONS

Cai M et al., "Novel 3D Pharmacophore of a-MSH/y-MSH Hybrids Leads to Selective Human MC1R and MC3R Analogues" Journal of Medicinal Chemistry, 2005, 48(6)1839-1848.

Cai M et al., "Cell Signaling and Trafficking of Human Melanocortin Receptors in Real Time Using Two-photon Fluorescence and Confocal Laser Microscopy: Differentiation of Agonists and Antagonists" Chemical Biology & Drug Design, 2006, 68(4):183-93.

Cannan RK and Kibrick A, "Complex Formation between Carboxylic Acids and Divalent Metal Cations" Journal o/the American Chemical Society, 1938, 60:2314-2320.

Chen J et al., "Melanoma-targeting Properties ofY9mTechnetium-labeled Cyclic u-Melanocyte-stimulating Hormone Peptide Analogues" Cancer Research, 2000, 60(20):5649-5658.

Chen J et al., "In vivo Evaluation of9YmTc/I?8Re-Labeled Linear Alpha-Melanocyte Stimulating Hormone Analogs or Specific Melanoma Targeting" Nuclear Medicine and Biology, 1999, 26(6):687-93.

Chrastina A et al., "Overcoming in vivo barriers to targeted nanodelivery" Interdisciplinary Reviews: Ianomedicine and Nanobiotechnology, 2011, 3(4):421-437.

Ehrlich J and Bogert MT, "Experiments in the Veratrole and Quinoxaline Groups" Journal o/Organic Chemistry, 1947, 12:522-534.

Hall JE et al., "Obesity-induced Hypertension: Role of Sympathetic Nervous System, Leptin, and Melanocortins" Journal 0/ Biological Chemistry, 2010, 285(23): 17271-17276.

Handl HL et al., "Lanthanide-based time-resolved fluorescence of in cyto ligand-receptor interactions" Analytical Biochemistry, 2004, 330(2):242-250.

Hu J et al., "Drug-Loaded and Superparamagnetic Iron Oxide Nanoparticle Surface-Embedded Amphiphilic Block copolymer Micelles for Integrated Chemotherapeutic Drug Delivery and MR Imaging" Langmuir, 2012, 28(4):2073-2082. Epub ahead of print(DOI: 1 0.1 021 II a203992q).

Jia Z et al., "One-Pot Conversion of RAFT-Generated Multifunctional Block Copolymers of HPMA to Doxorubicin conjugated Acid- and Reductant-Sensitive Crosslinked Micelles" Biomacromolecules, 2008, 9(11 ):31 06-3113.

Jun D-J et al., "Melanocortins induce interleukin 6 gene expression and secretion through melanocortin receptors 2 and 5 in 3T3-LI adipocytes" Journal of Molecular Endocrinology, 2010,44:225-236.

Kedar U et al., "Advances in polymeric micelles for drug delivery and tumor targeting" Nanomedicine: Nanotechnology, Biology and Medicine, 2010, 6:714-729.

Kell Y JM et al., "Immobilized a-melanocyte stimulating hormone 10-13 (GKPV) inhibits tumor necrosis factor-a stimulated NF-KB activity" Peptides, 2006, 27(2):431-437.

Kessinger C et al., "In vivo angiogenesis imaging of solid tumors by avp3-targeted, dual-modality micellar ianoprobes" Experimental Biology and Medicine, 2010, 235:957-965.

Kim S et al., "Overcoming the barriers in micellar drug delivery: loading efficiency, in vivo stability, and micelle-cell Interaction" Expert Opinion on Drug Delivery, 2010, 7(1):49-62.

Kim TH et al., "Evaluation of Temperature-Sensitive, Indocyanine Green-Encapsulating Micelles for Noninvasive Near-Infrared Tumor Imaging" Pharmaceutical Research, 2010, 27:1900-1913.

Koikov LN et al., "Sub-Nanomolar hMC1R Agonists by End-Capping of the Melanocortin Tetrapeptide His-D-Phe-Arg-Trp-NH2" Bioorganic & Medicinal Chemistry Letters, 2003, 13(16):2647-2650.

Koikov LN et al., Analogs of sub-nanomolar hMC1R agonist LK-184[Ph(CH2hCO-His-o-Phe-Arg-Trp-NH2J. An additional binding site within the human melanocortin receptor 1 T Bioorganic & Medicinal Chemistry Letters. 2004. 14:3997-4000.

Lee H et al., "The Effects of Particle Size and Molecular Targeting on the Intratumoral and Suncellular Distribution of Polymeric Nanoparticles" Molecular Pharmaceutics, 2010, 7(4)1195-1208.

Lee H et al., "In Vivo Distribution of Polymeric Nanoparticles at the Whole Body, Tumor and Cellular Levels" Pharmaceutical Research, 2010, 27(11):2343-2355.

Li J et al., "Redox-sensitive micelles self-assembled from amphiphilic hyaluronic acid-deoxycholic acid conjugates or targeted intracellular delivery of pac lit axel" Biomaterials, 2012, 33:2310-2320.

Li Y et al., "Well-Defined, Reversible Boronate Crosslinked Nanocarriers for Targeted Drug Delivery in Response to Acidic pH values and cis-Diols" Angewandte Chemie (International ed. in English), 2012 51:1-7.

Liu T et al., "Multifunctional pH-Disintegrable micellar nanoparticles of asymmetrically functionalized p-cyclodextrin-Based star copolymer covalently conjugated with doxorubicin and DOTA-Gd moieties" Biomaterials, 2012, 33:2521-2531.

Mayorov AV et al., "Effects of Macrocycle Size and Rigidity on Melanocortin Receptor-1 and -5 Selectivity in Cyclic Lactam a-Melanocyte-Stimulating Hormone Analogs" Chemical Biology & Drug Design, 2006, 67(5):329-335.

Oerlemans C et al., "Polymeric Micelles in Anticancer Therapy: Targeting, Imaging, and Triggered Release" Pharmaceutical Research, 2010, 27:2569-2589.

Poon Z et al., "Highly stable, ligand-clustered "patchy" micelle nanocarriers for systemic tumor targeting" Ianomedicine: Nanotechnology, Biology and Medicine, 2010, 7(2):201-209.

Rios-Doria J et al., "A Versatile Polymer Micelle Drug Delivery System for Encapsulation and In Vivo Stabilization of Hydrophobic Anticancer Drugs" Journal of Drug Delivery, 2012, 2012:951741, in press: Oct. 15, 2011.

Rodrigues AR et al., "Melanocortin 5 receptor activates ERKII2 through a PI3Kregulated signaling mechanism" Molecular and Cellular Endocrinology, 2009, 303:74-81.

Sawyer T et al., "4-Norleucine, 7-D-phenylalanine-a-melanocyte-stimulating hormone: A highly potent a-melanotropin with ultralong biological activity" Proceedings of the National Academy of Sciences, 1980, 77 10):5754-5758.

Sessler JL et al., "Texaphyrins: Synthesis and Applications" Accounts of Chemical Research, 1994, 27:43-50.

Sessler JL et al., "New texaphyrin-type expanded porphyrins" Pure and Applied Chemistry, 1996, 68(6):1291-1295.

Sessler JL and Miller RA? "Texaphyrins. New Drugs with Diverse Clinical Applications in Radiation and Photodynamic Therapy" Biochemical Pharmacology, 2000, 59:733-739.

Sessler JL et al., "Gadolinium(III) Texaphyrin: A Novel MRI Contrast Agent" Journal o/the American Chemical Society, 1993, 115(22):10368-10369.

Sessler JL et al., "Synthesis and Structural Characterization of Lanthanide(III) Texaphyrins" Inorganic Chemistry, 1993, 32:3175-3187.

Sessler JL et al., "An Expanded Porphyrin: The Synthesis and Structure of a New Aromatic Pentadentate Ligand" Journal o/the American Chemical Society, 1988, 110(16):5586-5588.

Shiraishi K et al., "Polyion complex micelle MRI contrast agents from Poly( ethylene glycol)-b-poly(L-lysine) block aopolymers having Gd-DOT A; preparations and their control of T]-relaxivities and blood circulation characteristics" Journal o/Controlled Release, 2010, 148:160-167.

Siegrist W et al., "Characterization of Receptors for a-Melanocyte-stimulating Hormone on Human Melanoma Cells" Cancer Research, 1989, 49(22):6352-6358.

Sun T-M et al., "Simultaneous Delivery of siRNA and Pacilitaxel via a "Two-in-One" Micelleplex Promotes Synergistic Tumor Supression" ACS Nano, 2011, 5(2): 1483-1494.

Tang N et al., "Improving Penetration in Tumors with Nanoassemblies of Phospholipids and Doxorubicin" Journal of the National Cancer Institute, 2007, 99(13): 1 004-1 015.

Todorovic A et al., "N-Terminal Fatty Acylated His-DPhe-Arg-Trp-NH2 Tetrapeptides: Influence of Fatty Acid Chain Length on Potency and Selectivity at the Mouse Melanocortin Receptors and Human Melanocytes" Journal of Medicinal Chemistry, 2005, 48:3328-3336.

(56) References Cited

OTHER PUBLICATIONS

Van Der Ploeg LHT et al., "A role for the melanocortin 4 receptor in sexual function" Proceedings of the National Academy of Sciences, 2002, 99( 17): 11381-11386.

Viala 1 et al., "Phase IB and II Multidose Trial of Gadolinium Texaphyrin, a Radiation Sensitizer Detectable at MR Imaging: Preliminary Results in Brain Metastases" Radiology, 1999, 212(3):755-759.

Webb TR and Clark AIL, "Minireview: The Melanocortin 2 Receptor Accessort Proteins" Molecular Endocrinology, 2010, 24(3):475-484.

Xiong X-B and La V Asanifar A, "Traceable Multifunctional Micellar Nanocarriers for Cancer-Targeted Co-delivery of MDR-I siRNA and Doxorubicin" ACS Nano, 2011, 5(6):5202-5213.

Yang Ret al., "Galactose-Decorated Cross-Linked Biodegradable Poly(ethyleneglycol)-b-poly( £-caprolactone) Block Copolymer Micelles for Enhanced Hepatoma-Targeting Delivery of Pac litaxe l" Biomacromolecules, 2011, 12:3047-3055.

Yang X et al., "Tumor-Targeting. pH-Responsive, and Stable Unimolecular Micelles as Drug Nanocarriers for Targeted Cancer Therapy" Bioconjugate Chemistry, 2010, 21 (3):496-504.

Yang Y et al., "Novel Binding Motif of ACTH Analogues at the Melanocortin Receptors" Biochemistry, 2009, 48:9775-9784.

Haskell-Leuvano et al. ("Structure activity studies of the melanocortin antagonist SHU9119 modified at the 6, 7, 8 and 3 positions" Peptides 21 (2000) 49-57).

Chatterjee et al. ("Synthesis of N-methylated cyclic peptide" Nature Protocols: 432 vol. 7(3) 2012).

Thermo Scientific Protein Glycosylation (available May 5, 2012).

Yokoyama M, "Clinical Applications of Polymeric Micelle Carrier Systems in Chemotherapy and Image Diagnosis of Solid Tumors" Journal of Experimental and Clinical Medicine, 2011, 3(4):151-158.

Young SW et al., "Gadolinium(III) texaphyrin: A tumor selective radiation sensitizer that is detectable by MRI" Proceedings of the National Academy of Sciences, 1996, 93:6610-6615.

Plitas G and Ariyan CE, "Controversies in the Management of Regional Nodes in Melanoma" Journal of the National Comprehensive Cancer Network, 2012, 10:414-421.

Koo H et al., "In Vivo Targeted Delivery of Nanoparticles for Theranosis" Accounts of Chemical Research, 2011, 44(10): 1 0 18-1 028.

Shabsigh et al., Current Urology Reports, 2:463-467, Nov. 2001.

Lee et al. "Solution Structures and Molecular Interactions of Selective Melanocortin Receptor Antagonists," Mol. Cells, Dec. 31, 2010 (Dec. 31, 2010). vol. 30, pp. 551-556.

Lucas Doeoens et al: Journal of the American Chemical Society, vol. 132, No. 23, Jun. 16, 2010, pp. 8115-8128, XP055389484.

Victor J. Hruby et al: Annual Review of Pharmacology and Toxicology., vol. 53, No. 1, Jan. 6, 2013, pp. 557-580, XP055389581.

Yaniv Linde: "Structure-activity relationship and metabolic stability studies of backbone cyclization and N-methylation of melanocortin peptides—Linde—2008—Peptide Science—Wiley Online Library", Jul. 24, 2008, XP055389491, Retrieved from the Internet: URL:http://onlinelibrary.wiley.com/doi/10.1002/bip. 21057/full [retrieved on Jul. 10, 2017].

Zingsheim, Structure-Activity Study of a-N-Methylated SHU9119 Analogues, hMC4R/TNF-a Antagonists, and Mutational Studies of the Melanocyte Stimulating Hormone Receptor, from The University of Arizona, OS/2009, pp. 1-66.

* cited by examiner

METHODS FOR THE TREATMENT OF DEPRESSION AND ANXIETY

CROSS REFERENCE

This application is a non-provisional and claims benefit of U.S. Provisional Patent Application No. 62/242,850, filed Oct. 16, 2015, the specification(s) of which is/are incorporated herein in their entirety by reference.

This application is a continuation-in-part and claims benefit of U.S. Patent Application No. PCT/US15/35180, filed Jun. 10, 2015, which claims benefit of U.S. Provisional Patent Application No. 62/017,137, filed Jun. 25, 2014, and U.S. patent application Ser. No. 14/300,991, filed Jun. 10, 2014, the specification(s) of which is/are incorporated herein in their entirety by reference.

FIELD OF THE INVENTION

The present invention relates to methods of treating depression or anxiety, in particular, treating depression or anxiety with a selective melanocortin 5 receptor (MC5R) antagonist.

BACKGROUND OF THE INVENTION

Depression and anxiety disorders are some of the most common mental illnesses. Although the two are different, depression and anxiety can occur together and can have similar treatments. These disorders can be treated through psychotherapy and medications, such as anti-depressants and anti-anxiety medications. Unfortunately, current medications may take weeks to months to achieve their full effects and in the meantime, patients continue to suffer from their symptoms and continue to be at risk. Moreover, side effects from these medications can range from unpleasant to life-threatening; for instance, there can be an increased risk of suicide, hostility, and even homicidal behavior. Pharmacological treatments that have a rapid onset of antidepressant or anti-anxiety effects within hours or a few days and that are sustained are therefore desired.

Currently, there is no single effective treatment for depression, anxiety, and other related diseases. Hence, there remains a need for improved treatments of depression, anxiety and/or other related diseases that provide increased efficacy and reduces or eliminates any potential side effects.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

As will be described herein, one embodiment of the subject disclosure features a method of treating a depressive disorder or an anxiety disorder in a subject in need of such treatment. The method may comprise administering to the subject a therapeutically effective amount of a composition comprising Ac-Nle$^4$-c[Asp$^5$-His$^6$-(NMe)D-Nal(2')$^7$-Arg$^8$-Trp$^9$-(NMe)Lys$^{10}$]-NH$_2$ (PEPTIDE 9), in a pharmaceutically acceptable carrier.

DESCRIPTION OF PREFERRED EMBODIMENTS

Figure 1:
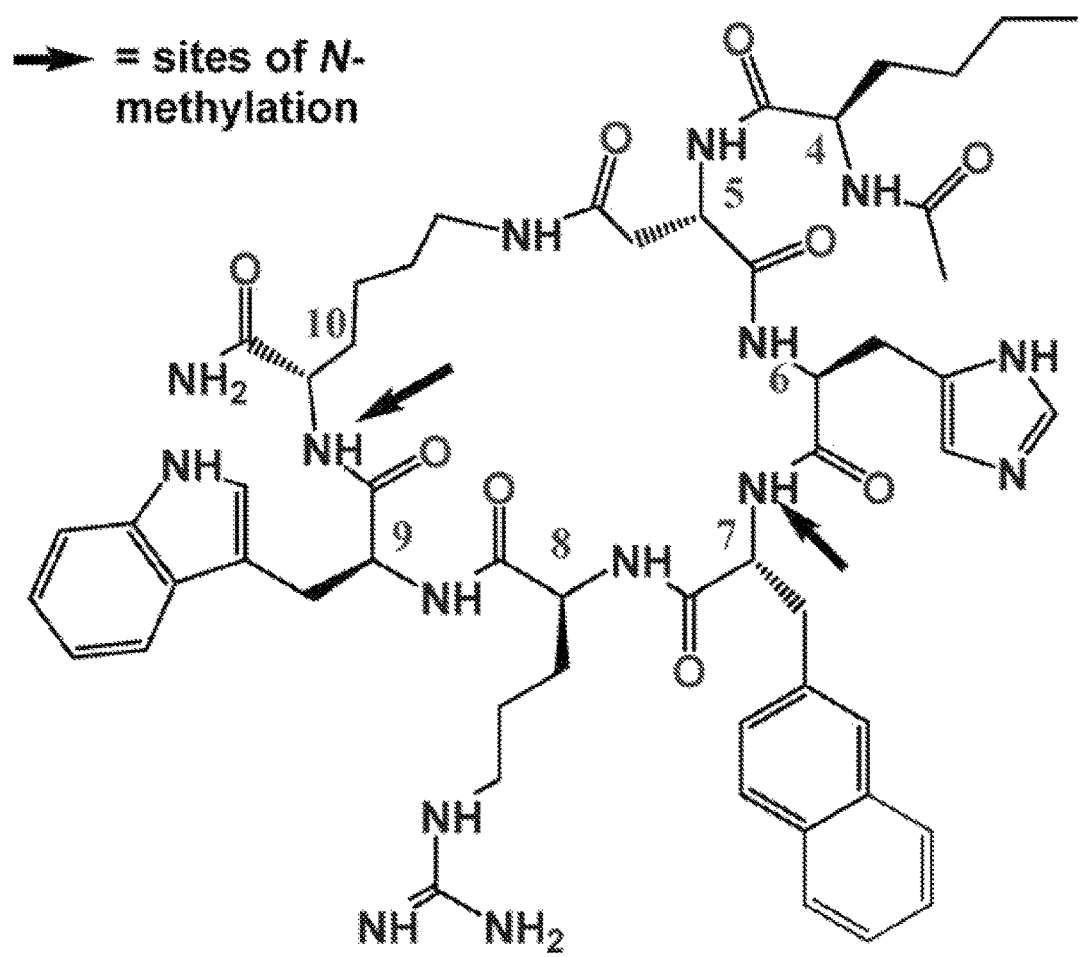
FIG. 1 shows a structure of SHU 9119. The two arrows indicate the sites of N-methylation of the backbone NHs to synthesize the PEPTIDE 9 analogue.

Before the present method is disclosed and described, it is to be understood that this invention is not limited to specific methods, as such may, of course, vary. It is also to be understood that the terminology used herein is for the purpose of describing particular embodiments only and is not intended to be limiting.

As defined herein, the term "antagonist" refers to compound that diminishes a response. The antagonist binds to the same site as the endogenous compound and diminishes or blocks the signal generated by the endogenous agent.

As defined herein, the term "N-methylation" refers to a form of alkylation wherein a methyl group, CH$_3$, replaces the hydrogen atom of the NH moiety in the backbone amide NHs of peptides.

As used herein, the term "NMe" preceding any three-letter abbreviation for an amino acid, i.e. (NMe)Lys, denotes the N-methylated form of the amino acid. As used herein, the term "Nle" refers to a Norleucine.

In some embodiments, the present invention may feature a method of treating a depressive disorder or an anxiety disorder in a subject in need of such treatment. According to one embodiment, the method may comprise administering to the subject a therapeutically effective amount of a composition comprising: Ac-Nle$^4$-c[Asp$^5$-His$^6$-(NMe)D-Nal(2')$^7$-Arg$^8$-Trp$^9$-(NMe)Lys$^{10}$]-NH$_2$ (PEPTIDE 9), in a pharmaceutically acceptable carrier.

Preferably, the administration of the composition is effective to evoke at least one of a psychostimulating effect, an anxiolytic effect, or an antidepressant effect. Moreover, when the composition is administered to the subject, clinical improvement may be observed in about 1 to 7 days or about 1 to 14 days.

According to another embodiment, the present invention may feature a method of treating a depressive disorder in a subject in need of such treatment. In some embodiments, the method may comprise administering to the subject a therapeutically effective amount of a composition comprising: Ac-Nle$^4$-c[Asp$^5$-His$^6$-(NMe)D-Nal(2')$^7$-Arg$^8$-Trp$^9$-(NMe)Lys$^{10}$]-NH$_2$ (PEPTIDE 9), in a pharmaceutically acceptable carrier. Preferably, administration of the composition can treat the depressive disorder in the subject such that clinical improvement is observed in about 1 to 7 days or about 1 to 14 days.

In some embodiments, the subject may be a mammal, such as a human. In other embodiments, the PEPTIDE 9 is administered in a dosage of about 0.001 mg/kg to 100 mg/kg of body weight. For instance, the dosage can be about 0.001-5 mg/kg of body weight, or about 5-10 mg/kg of body weight, or about 10-20 mg/kg of body weight, or about 20-40 mg/kg of body weight, or about 40-60 mg/kg of body weight, or about 60-80 mg/kg of body weight, or about 80-100 mg/kg of body weight. In other embodiments, the composition is administered twice a day, daily, or every other day. In still other embodiments, the composition may be administered intranasally, intravenously, transdermally, or orally.

Examples of depressive disorders may include, but are not limited to, major depressive disorders or persistent depressive disorders. Examples of anxiety disorders may include, but are not limited to, generalized anxiety disorders or panic disorders.

Alternative embodiments for treating the depressive disorder or anxiety disorder in the subject may include administering the composition is combination with a non-pharmacological treatment. Examples of non-pharmacological treatments may include, but are not limited to, is psychotherapy, electroconvulsive therapy, transcranial magnetic stimulation, vagus nerve stimulation, acupuncture, hypnosis, meditation, an exercise regimen, and administration of naturopathic herbs and supplements.

Figure 2:
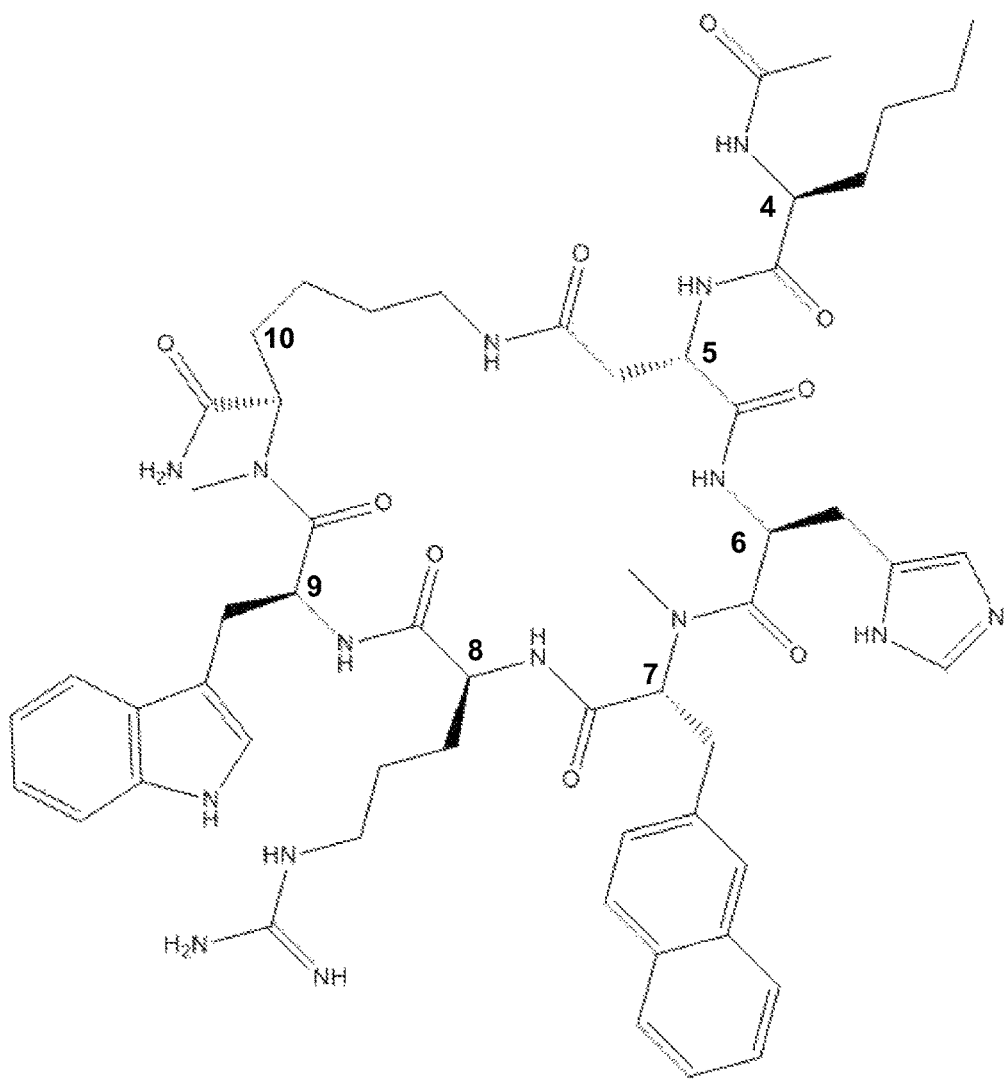
FIG. 2 shows a structure of PEPTIDE 9.

Referring now to FIGS. 1 and 2, PEPTIDE 9 is a di-methylated analogue of a cyclic lactam heptapeptide SHU9119, Ac-Nle$^4$-c[(Asp$^5$-His$^6$-D-Nal(2')$^7$-Arg$^8$-Trp$^9$-Lys$^{10}$]-NH$_2$, in which the D-Nal(2')$^7$ and Lys$^{10}$ are N-methylated. Further details of PEPTIDE 9 are provided in commonly-assigned and co-pending PCT/US15/35180 filed on Jun. 10, 2015, which is hereby incorporated by reference. Relevant sections of the incorporated patent application describe that the combination of (NMe)D-Nal(2')$^7$ and (NMe)Lys$^{10}$ (Peptide 9) results in a very selective antagonist for the hMC5R.

The MC5R may be present in the central nervous system (CNS), but its function in this location is not completely understood. Without wishing to limit the invention to a particular theory or mechanism, since PEPTIDE 9 is a selective MC5R antagonist, then PEPTIDE 9 may be potentially therapeutic for treating depression and anxiety.

Disclosed are the various compounds, solvents, solutions, carriers, and/or components to be used to prepare the compositions to be used within the methods disclosed herein. Also disclosed are the various steps, elements, amounts, routes of administration, symptoms, and/or treatments that are used or observed when performing the disclosed methods, as well as the methods themselves. These and other materials, steps, and/or elements are disclosed herein, and it is understood that when combinations, subsets, interactions, groups, etc. of these materials are disclosed, that while specific reference of each various individual and collective combination and permutation of these compounds may not be explicitly disclosed, each is specifically contemplated and described herein.

As used herein, a major depressive disorder (MDD) is a common disorder of mood and affect characterized by one or more major depressive episodes. These episodes are defined diagnostically using a criteria-based syndrome listed and described in literature as would be known to one of ordinary skill in the art. These episodes are diagnosed in a human patient if the patient has experienced 5 symptoms from a list of 9 symptom categories every day, or nearly every day, for a period lasting at least 2 weeks. At least one symptom must be present from either category 1 (having a sad, depressed, empty, or irritable mood, or appearing sad to others), or category 2 (experiencing loss of interest in or pleasure from activities). The other symptom categories include: 3) change in weight and/or appetite, 4) insomnia or hypersomnia, 5) psychomotor agitation or retardation, 6) fatigue and/or loss of energy, 7) feelings of worthlessness and/or excessive or inappropriate guilt, 8) diminished ability to think or of concentrate and/or indecisiveness, and 9) recurrent thoughts of death or suicide.

Persistent depressive disorder, also known as dysthymia, is a chronic (ongoing) type of depression in which a person's moods are regularly low. However, the symptoms are not as severe as with major depression.

Bipolar Disorder (also known as "manic-depressive illness") is a mood disorder arising in a human patient who experiences major depressive episodes which alternate with episodes of mania (in the case of type I) or hypomania (in the case of type II). Mania is a syndrome characterized by a euphoric, expansive, or irritable mood lasting at least one week. In addition, at least three of the following symptoms persisted during the same time period: inflated self esteem and/or grandiosity, decreased need for sleep, increased volume or rate of speech, flight of ideas and/or racing thoughts, distractibility, increased goal-directed activity and/or psychomotor agitation, excessive involvement in pleasurable activities that have a high potential for painful consequences. Mania and hypomania have similar signs and symptoms but are distinguished by the degree to which they result in impaired social and occupational functioning.

Bipolar affective disorder is characterized by two or more episodes in which the patient's mood and activity levels are significantly disturbed, this disturbance consisting on some occasions of an elevation of mood and increased energy and activity (hypomania or mania) and on others of a lowering of mood and decreased energy and activity (depression). Repeated episodes of hypomania or mania only are classified as bipolar. This includes manic depressive illness, psychosis, and reaction. This excludes bipolar disorder, single manic episode and cyclothymia.

In Bipolar affective disorder, current episode mild or moderate depression, the patient is currently depressed, as in a depressive episode of either mild or moderate severity, and has had at least one authenticated hypomanic, manic, or mixed affective episode in the past.

In Bipolar affective disorder, current episode severe depression without psychotic symptoms, the patient is currently depressed, as in severe depressive episode without psychotic symptoms, and has had at least one authenticated hypomanic, manic, or mixed affective episode in the past.

Treatment-resistant depression is exemplified by a case in which a human patient with either major depressive disorder or bipolar disorder continues to meet criteria for a major depressive episode in spite of treatment with conventional antidepressant drugs at adequate doses and treatment durations (at least 4 to 8 weeks).

Panic Disorder is an episodic paroxysmal anxiety syndrome characterized by recurrent attacks of severe anxiety (panic) which are not restricted to any particular situation or set of circumstances and are therefore unpredictable. The symptoms include sudden onset of palpitations, chest pain, dyspnea, dizziness, and feelings of unreality (depersonalization or derealization). There is often also a secondary fear of dying, losing control, or going insane. Panic disorder may be seen with or without agoraphobia, which is characterized by a cluster of phobias embracing fears of leaving home, entering shops, crowds and public places, or traveling alone in trains, buses or planes. Avoidance of the phobic situation is prominent, to an extent that agoraphobics alter their lifestyles to avoid their relevant phobic situations.

Social phobia (also called Social Anxiety Disorder) is characterized by a marked and persistent fear of one or more social or performance settings in which the patient is exposed to unfamiliar people or to possible scrutiny by other people. The patient fears that in such situation they will act in a way (or show anxiety symptoms) that will be humiliating or embarrassing. Exposure to the feared social situation almost invariably provokes anxiety, and this response may progress to panic attacks. The feared social or performance situations are avoided, or else are endured with intense anxiety and distress.

Post-traumatic stress disorder arises as a delayed or protracted response to a stressful event or situation (of either brief or long duration) of an exceptionally threatening or catastrophic nature which is likely to cause pervasive distress in almost anyone. Predisposing factors, such as personality traits or previous history of mood or anxiety disorders, may lower the threshold for the development of the syndrome or aggravate its course, but they are neither necessary nor sufficient to explain its occurrence. Typical features include episodes of repeated reliving of the trauma in intrusive memories ("flashbacks"), dreams or nightmares occurring against the persisting background of a sense of "numbness" and emotional blunting, detachment from other people, unresponsiveness to surroundings, anhedonia, and avoidance of activities and situations reminiscent of the trauma. There often is a state of autonomic hyperarousal with hypervigilance, an enhanced startle reaction, and insomnia. Anxiety and depression commonly are associated with these symptoms and signs. The onset follows the trauma with a latency period that may range from a few weeks to months.

Generalized anxiety disorder is a chronic anxiety syndrome characterized by excessive worry or anxiety over a period lasting at least 6 months. These symptoms are associated with at least 3 of the following 6 symptoms: 1) restlessness or feeling on edge, 2) feeling easily fatigued, 3) impaired concentration, 4) irritability, 5) muscle tension, and 6) sleep disturbance. These anxiety symptoms are generalized and persistent but not restricted to, or even strongly predominating in, any particular environmental circumstances. The anxiety syndrome is sufficiently severe to cause clinically significant distress or to impair social or occupational functioning.

A "subject" is an individual and includes, but is not limited to, a mammal (e.g., a human, horse, pig, rabbit, dog, sheep, goat, non-human primate, cow, cat, guinea pig, or rodent), a fish, a bird, a reptile or an amphibian. The term does not denote a particular age or sex. Thus, adult and newborn subjects, as well as fetuses, whether male or female, are intended to be included. A "patient" is a subject afflicted with a disease or disorder. The term "patient" includes human and veterinary subjects.

The terms "administering" and "administration" refer to methods of providing a pharmaceutical preparation to a subject. Such methods are well known to those skilled in the art and include, but are not limited to, administering the compositions orally, parenterally (e.g., intravenously and subcutaneously), by intramuscular injection, by intraperitoneal injection, intrathecally, transdermally, extracorporeally, topically or the like.

The term "antidepressant effect" is used in the conventional sense. It is associated with a reversal of or a reduction in the severity of a depressed mood or state of mind.

The term "anxiolytic effect" is used in the conventional sense. It is associated with an inhibition, a reversal of, a reduction in the severity of symptoms of anxiety.

The term "psychostimulating effect", as the term implies, is associated in an increase or improvement in the overall level of mental activity. It is related to patients exhibiting nervous behavior, or having unpleasant feelings of dread, or lacking energy, drive and desire, or lacking concentration and memory,. Common psychostimulating effects may include, but are not limited to, enhanced alertness, awareness, wakefulness, endurance, productivity, motivation, increased arousal, and locomotion (i.e. movement or increased energy). The psychostimulants may also be capable of improving mood and relieving anxiety, and can even induce feelings of euphoria.

A composition can also be administered by topical intranasal administration (intranasally) or administration by inhalant. As used herein, "topical intranasal administration" means delivery of the compositions into the nose and nasal passages through one or both of the nares and can comprise delivery by a spraying mechanism (device) or droplet mechanism (device), or through aerosolization of the composition. Administration of the compositions by inhalant can be through the nose or mouth via delivery by a spraying or droplet mechanism. As used herein, "an inhaler" can be a spraying device or a droplet device for delivering a composition comprising PEPTIDE 9, in a pharmaceutically acceptable carrier, to the nasal passages and the upper and/or lower respiratory tracts of a subject. Delivery can also be directly to any area of the respiratory system (e.g., lungs) via intratracheal intubation. The exact amount of the compositions required will vary from subject to subject, depending on the species, age, weight and general condition of the subject, the severity of the disorder being treated, the particular composition used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, for example, U.S. Pat. No. 3,610,795, which is incorporated by reference herein.

A "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products.

As described above, the compositions can be administered to a subject in a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans, including solutions such as sterile water, saline, and buffered solutions at physiological pH. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semi-permeable matrices of solid hydrophobic polymers containing the disclosed compounds, which matrices are in the form of shaped articles, e.g., films, liposomes, microparticles, or microcapsules. It will be apparent to those persons skilled in the art that certain carriers can be more preferable depending upon, for instance, the route of administration and concentration of composition being administered. Other compounds can be administered according to standard procedures used by those skilled in the art.

Pharmaceutical formulations can include additional carriers, as well as thickeners, diluents, buffers, preservatives, surface active agents and the like in addition to the compounds disclosed herein. Pharmaceutical formulations can also include one or more additional active ingredients such as antimicrobial agents, anti-inflammatory agents, anesthetics, and the like.

The pharmaceutical formulation can be administered in a number of ways depending on whether local or systemic treatment is desired, and on the area to be treated. Administration may be topically (including ophthahnically, vaginally, rectally, intranasally), orally, by inhalation, or parenterally, for example by intravenous drip, subcutaneous, intraperitoneal or intramuscular injection. The disclosed compounds can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, fish oils, and injectable organic-esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Pharmaceutical formulations for oral administration include, but are not limited to, powders or granules, suspensions or solutions in water or non-aqueous media, capsules, sachets, or tablets. Thickeners, flavorings, diluents, emulsifiers, dispersing aids or binders may be desirable.

In one aspect, PEPTIDE 9 can be administered in an intravenous dosage. This dosage can be administered to a subject once daily or in divided dosages throughout a day, as determined by methods known in the art. This dosage can be administered to a subject for one day and then stopped if the subject responds immediately, or the dosage can be administered on a daily basis until a clinical response is noted. It is contemplated that the dosage of PEPTIDE 9, can be administered as infrequently as once every month or every two months, or at any interval in between, depending on a subject's clinical response to the medication. Thus, if a subject responds to one dosage of PEPTIDE 9, a person of skill may determine that further dosages of the medication can be withheld. Moreover, if a subject does not respond to the initial dosage and administration of PEPTIDE 9, a person of skill can administer the medication daily for several days until such response occurs. A person of skill can monitor a subject's clinical response to the administration of PEPTIDE 9, and administer additional dosages if the subject's mood disorder symptoms reappear after a period of remission. It is contemplated that PEPTIDE 9, can be administered to a subject with, for example, major mood disorder on a daily basis, on an alternating daily basis, on a weekly basis, on a monthly basis, or at any interval in between.

In another aspect, PEPTIDE 9 can be administered to a subject transdermally, by using an adherent patch, by using iontophoresis, or by using any other method known to a person of skill. The dosage of PEPTIDE 9, administered transdermally can be given daily or infrequently as once every 1 to 4 weeks. A person of skill, monitoring a subject's clinical response and improvement, can determine the frequency of administration of the medication by methods known in the art.

In another aspect, PEPTIDE 9 can be administered to a subject intranasally in a dosage taken once daily or in divided doses. The medication can be administered for one day and then stopped if clinical improvement occurs rapidly. Further, the medication can be administered as infrequently as once every 1 to 4 weeks. A person of skill, monitoring a subject's clinical response to the administration of the medication, can adjust the frequency of administration according to methods known in the art.

In another aspect, PEPTIDE 9 can be administered to a subject intramuscularly in a dosage taken once daily or in divided doses. The medication can be administered for one day and then stopped if clinical improvement occurs rapidly. Furthermore, the medication can be administered as infrequently as once every 1 to 4 weeks. A person of skill, monitoring a subject's clinical response, can adjust the frequency of administration of the medication according to methods known in the art.

In still another aspect, PEPTIDE 9 can be administered to a subject orally in a dosage taken once daily or in divided doses. The medication can be administered for one day and then stopped if clinical improvement occurs rapidly. Furthermore, the medication can be administered as infrequently as once every 1 to 4 weeks. A person of skill, monitoring a subject's clinical response, can adjust the frequency of administration of the medication according to methods known in the art.

EXAMPLES

The following examples are included to demonstrate certain embodiments of the invention. It should be appreciated by those of skill in the art that the techniques disclosed in the examples which follow represent techniques discovered by the inventors to function well in the practice of the invention, and thus are considered to constitute certain aspects for its practice. However, those of skill in the art should, in light of the present disclosure, appreciate that many changes can be made in the specific embodiments which are disclosed and still obtain a like or similar result without departing from the spirit and scope of the invention.

Example 1

Repeated Administration of a Fixed Dose IV

The following example describes a treatment strategy for depression involving the repeated administration of PEPTIDE 9.

A 52 year old female has a strong family history of depression and has had disabling depression since her teens. She has been tried on numerous oral medications without benefit. At times she is agitated and has panic attacks, which fluctuates with lethargy and insomnia. She is referred to a neurologist, who rules out any secondary causes for her symptoms. Her brain MRI scan and routine lab testing is within normal limits. Her psychiatrist recommends a trial of PEPTIDE 9 administered intravenously. A fixed IV of a PEPTIDE 9 dose (1 mg/kg infusion over 30 minutes) is repeated administered every two days over a two to three week period in hospital. A follow up visit with her psychiatrist reveals improving depression symptoms with less agitation, improved energy levels and sleep patterns. A second treatment of the fixed IV of a PEPTIDE 9 is given two months later. The patient continues to improve and is functioning normally at 6 months. No side effects are reported.

Example 2

Transdermal Administration of PEPTIDE 9

The following example describes treatment strategies for depression involving transdermal administration of PEPTIDE 9.

Six weeks after a 30 year old female gives birth to her first child, a follow up appointment with her obstetrician reveals that she is suffering from post-partum depression. The patient is experiencing excessive crying, difficulty bonding with her baby, excess sleeping, overwhelming fatigue, intense anger and sadness, and severe anxiety and panic attacks. She further reports that in some instances, she has thoughts of suicide and harm coming to her baby. The female takes the Edinburgh Post Natal Depression Scale (EPDS) test, in which she scores a 25. A score of 10 or greater indicates possible perinatal mood or anxiety disorder. Her obstetrician refers her to a psychiatrist, who officially diagnoses her with postpartum depression. The psychiatrist recommends a trial of PEPTIDE 9 administered using a transdermal patch. The patient is given a patch comprising a PEPTIDE 9 dose of 20 mg for transdermal delivery over a period 24 hours. A patch is to be administered every day for two weeks, followed by a visit with her psychiatrist. During her follow up visit with her psychiatrist, the patient retakes the EPDS test and scores a 12. She reports that her symptoms have drastically lessened in the past two weeks. Her psychiatrist prescribes another treatment of a transdermal patch comprising a PEPTIDE 9 dose of 10 mg for transdermal delivery over a period 24 hours. The patch is to be administered every other day for two weeks, followed by a visit with her psychiatrist. The patient continues to improve and is no longer suffering from post-partum depression 6 months later. No side effects are reported.

Example 3

Oral Administration of PEPTIDE 9

The following example describes treatment strategies for depression and anxiety involving oral administration of PEPTIDE 9.

A 50-year-old Caucasian male reports to his psychiatrist that he is feeling depressed and having panic attacks. He reveals that these symptoms began after his divorce. His psychiatrist prescribes an oral medication of a formulation comprising PEPTIDE 9 in a dose of 10 mg per tablet. The patient is to take the tablet twice a day for one month. The patient is highly responsive and experiences a reduction in his symptoms during the initial treatment period. After the initial treatment, the patient is prescribed to take a tablet of 5 mg of PEPTIDE 9 once a day for another month. The patient continues to improve and is functioning normally at three months. No side effects are reported.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A method of treating a depressive disorder or an anxiety disorder in a subject in need thereof, said method comprising administering to the subject a therapeutically effective amount of a composition comprising:

Ac-Nle$^4$-c[Asp$^5$-His$^6$-(NMe)D-Nal(2')$^7$-Arg$^8$-Trp$^9$-(NMe)Lys$^{10}$]-NH$_2$ (PEPTIDE 9), in a pharmaceutically acceptable carrier.

2. The method of claim 1, wherein the subject s a mammal.

3. The method of claim 1, wherein the subject is a mammal, wherein the mammal is a human.

4. The method of claim 1, wherein PEPTIDE 9 is an antagonist of melanocortin 5 receptor (MC5R).

5. The method of claim 1, wherein PEPTIDE 9 is administered in a dosage of about 0.001 mg/kg to 100 mg/kg of body weight.

6. The method of claim 5, wherein the composition is administered twice a day, daily, or every other day.

7. The method of claim 1, wherein the composition is administered intranasally, intravenously, transdermally, or orally.

8. The method of claim 1, wherein administration of the composition is combined with a non-pharmacological treatment for treating the depressive disorder or anxiety disorder in the subject.

9. The method of claim 8, wherein the non-pharmacological treatment is psychotherapy, electroconvulsive therapy, transcranial magnetic stimulation, vagus nerve stimulation, acupuncture, hypnosis, meditation, an exercise regimen, or combinations thereof.

10. A method of treating a depressive disorder in a subject in need thereof, said method comprising administering to the subject a therapeutically effective amount of a composition comprising:

Ac-Nle$^4$-c[Asp$^5$-His$^6$-(NMe)D-Nal(2')$^7$-Arg$^8$-Trp$^9$-(NMe)Lys$^{10}$]-NH$_2$ (PEPTIDE 9), in a pharmaceutically acceptable carrier.

11. The method of claim 10, wherein the subject is a mammal.

12. The method of claim 10, wherein the subject is a mammal, wherein the mammal is a human.

13. The method of claim 10, wherein PEPTIDE 9 is an antagonist of melanocortin 5 receptor (MC5R).

14. The method of claim 10, wherein PEPTIDE 9 is administered in a dosage of about 0.001 mg/kg to 100 mg/kg of body weight.

15. The method of claim 14, wherein the composition is administered twice a day, daily, or every other day.

16. The method of claim 10, wherein the composition is administered intranasally, intravenously, transdermally, or orally.

17. The method of claim 10, wherein administration of the composition is combined with a non-pharmacological treatment for treating the depressive disorder or anxiety disorder in the subject.

18. The method of claim 17, wherein the non-pharmacological treatment is psychotherapy, electroconvulsive therapy, transcranial magnetic stimulation, vagus nerve stimulation, acupuncture, hypnosis, meditation, an exercise regimen, or combinations thereof.

* * * * *